(12) United States Patent
Zhou et al.

(10) Patent No.: US 10,780,271 B2
(45) Date of Patent: Sep. 22, 2020

(54) SYSTEM AND METHOD FOR PERCEIVING SMELL REMOTELY

(71) Applicants: Lucas Mingzhi Zhou, LaGrangeville, NY (US); Lin Zhou, LaGrangeville, NY (US); Christopher Li, Poughquag, NY (US)

(72) Inventors: Lucas Mingzhi Zhou, LaGrangeville, NY (US); Lin Zhou, LaGrangeville, NY (US); Christopher Li, Poughquag, NY (US)

( * ) Notice: Subject to any disclaimer, the term of this patent is extended or adjusted under 35 U.S.C. 154(b) by 214 days.

(21) Appl. No.: 15/788,897

(22) Filed: Oct. 20, 2017

(65) Prior Publication Data
US 2018/0110981 A1 Apr. 26, 2018

Related U.S. Application Data

(60) Provisional application No. 62/496,517, filed on Oct. 21, 2016.

(51) Int. Cl.
| | | |
|---|---|---|
| *A61B 5/04* | (2006.01) | |
| *A61N 1/36* | (2006.01) | |
| *A61N 1/04* | (2006.01) | |
| A61B 5/0484 | (2006.01) | |
| *G06N 20/00* | (2019.01) | |

(52) U.S. Cl.
CPC ....... *A61N 1/36031* (2017.08); *A61N 1/0456* (2013.01); *A61N 1/0476* (2013.01); *A61N 1/0484* (2013.01); *A61N 1/36014* (2013.01); *A61N 1/36034* (2017.08); *A61B 5/04847* (2013.01); *A61N 1/3601* (2013.01); *G06N 20/00* (2019.01)

(58) Field of Classification Search
USPC .......................................................... 607/45
See application file for complete search history.

(56) References Cited

U.S. PATENT DOCUMENTS

| | | | | |
|---|---|---|---|---|
| 2003/0207337 | A1* | 11/2003 | Han | C07K 14/705 435/7.2 |
| 2010/0198281 | A1* | 8/2010 | Chang | A61K 9/0009 607/3 |
| 2012/0109241 | A1* | 5/2012 | Rauscher | A61B 5/40 607/9 |
| 2013/0066392 | A1* | 3/2013 | Simon | A61N 1/40 607/45 |
| 2015/0018706 | A1* | 1/2015 | Segal | A61B 5/0476 600/544 |
| 2016/0012749 | A1* | 1/2016 | Connor | G09B 5/00 600/13 |

* cited by examiner

*Primary Examiner* — Nicole F Lavert
(74) *Attorney, Agent, or Firm* — Scully, Scott, Murphy & Presser, P.C.

(57) ABSTRACT

Technology for the transition of light and sound over long distances, e.g. TV and radio, has revolutionized society. On the contrary, the technology to perceive a smell remotely is in its infancy, and has severe limitations such as latency, residual and infidelity. A system and methods are disclosed to allow smells to be perceived remotely. It is based on the brain waves associated with the olfactory bulb.

7 Claims, 4 Drawing Sheets

SYSTEM AND METHOD FOR PERCEIVING SMELL REMOTELY

FIELD

The present application relates generally to transmitting smell to a remote recipient and restore the smell in the recipient's olfactory bulb.

BACKGROUND

Since the early 20th century, people have wondered how to allow audiences to "smell the action". One of the first attempts to enable this was made by Arthur Mayer. In 1929, during a showing of The Broadway Melody, he installed a machine that was designed to puff out aromas when the corresponding image appeared on screen. A similar piece of technology, the Smell-O-Vision, debuted in the 1960's and was designed to do a similar task. Both machines failed. When released, the clouds of aromas took a few seconds to reach the viewers. By that time, the objects they were supposed to represent had already disappeared from the screen, arousing many complaints.

Despite these early failures, over time, technology in this field has improved. In June of 2011, the Jacobs School at the University of California published an article about three of their researchers and their invention. According to the article, Prof. Sungho Jin and graduate students Calvin Gardner and Hyunsu Kim have developed a " . . . compact device small enough to fit on the back of your TV with potentially thousands of odors" that runs on an X-Y matrix.

The OPhone Duo follows the same general idea as the gadget described above, but is already on the market and is made for iPhone. As the name suggests, the OPhone Duo comes in two parts: the OPhone app called OSnap and the OPhone device where the aromas are puffed out of. With the app, a user can take a picture of something and tag it with any combination of the available scents. After the message or ONote is addressed and sent, the ONote goes through OPhone's servers and is sent to the recipient OPhone. Once activated, the OPhone will release puffs of the aromas the message tags call for in short 10-second intervals, allowing the recipient to scent what the sender is smelling. The primary con of the OPhone is the need for a separate, large device in order for the system to work. Another con is that when a message has multiple tags, it is only able to puff each scent out one at a time instead of combining scents. While this may have solved the "cloud of smells" problem other technologies had, the OPhone is unable to combine when needed. On the flip side, the OPhone offers an elegant, rechargeable way to use a piece of new technology.

BRIEF SUMMARY

The methods and systems described herein provide ways to transmitting smell to a remote recipient and restore the smell in the recipient's olfactory bulb.

In an aspect of the present disclosure, a system is disclosed comprising a neuro connector that collects brain waves from an olfactory bulb and applies electric waves to an olfactory bulb, a smart chip that converts the brain waves into a digital file and converts a digital file into electric waves, a transceiver that transmits and receives the digital file, a power supply that provides energy to the system, a set of conductive wires that make electric connection among the neuro-connector, smart chip, transceiver, and power supply, and a head band where neuro-connector, smart chip, transceiver, power supply, and set of conductive wires are attached and it can be worn on the head of users.

In an aspect of the present disclosure, a method is disclosed including converting brain waves stimulated by an odorant into a digital smell file.

In an aspect of the present disclosure, a method is disclosed including converting a digital smell file into electric waves to stimulate the olfactory bulb for restoring the smell associated with the digital smell file.

In aspects of the present disclosure apparatus, systems, and computer program products in accordance with the above aspect may also be provided.

Further features as well as the structure and operation of various embodiments are described in detail below with reference to the accompanying drawings. In the drawings, like reference numbers indicate identical or functionally similar elements.

DETAILED DESCRIPTION

The methods, systems, and computer program products described herein may collect brain wave, convert the brain waves into a digital smell file, transmit the digital smell file to a recipient's system, convert the digital smell file to electric waves, apply the electric waves to recipient's olfactory bulb, and restore the smell in recipients' olfactory bulb.

Figure 1:
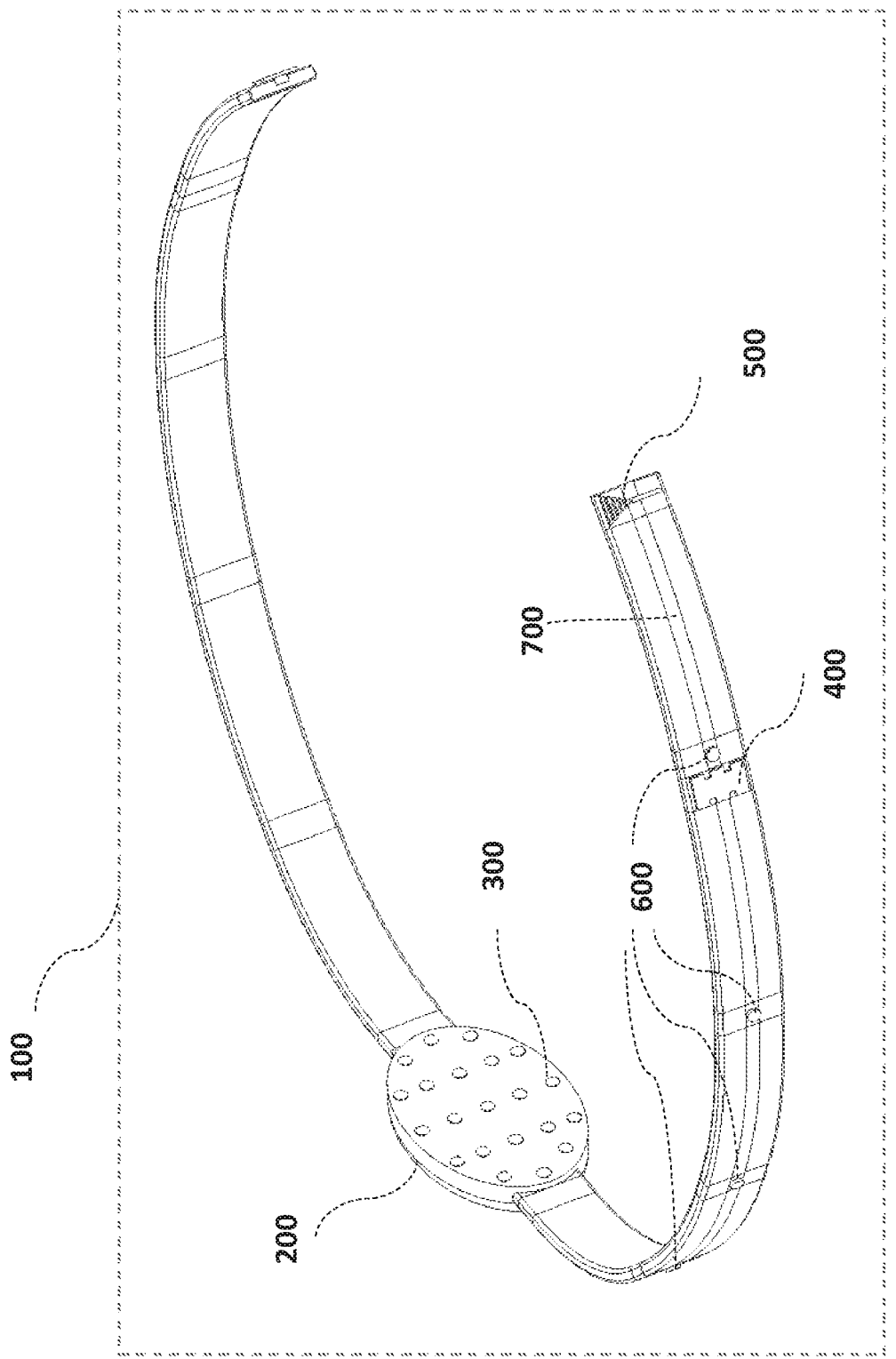
FIG. 1 is a side view of a system.

Referring now to FIG. 1, a system 100 is disclosed. System 100 may include, for example, a neuro connector 200, a smart chip 400, a transceiver 500, indicators 600, and a set of conductive wires 700. The neuro connector 200 may include, for example, at least a set of electrodes 300.

Figure 2:
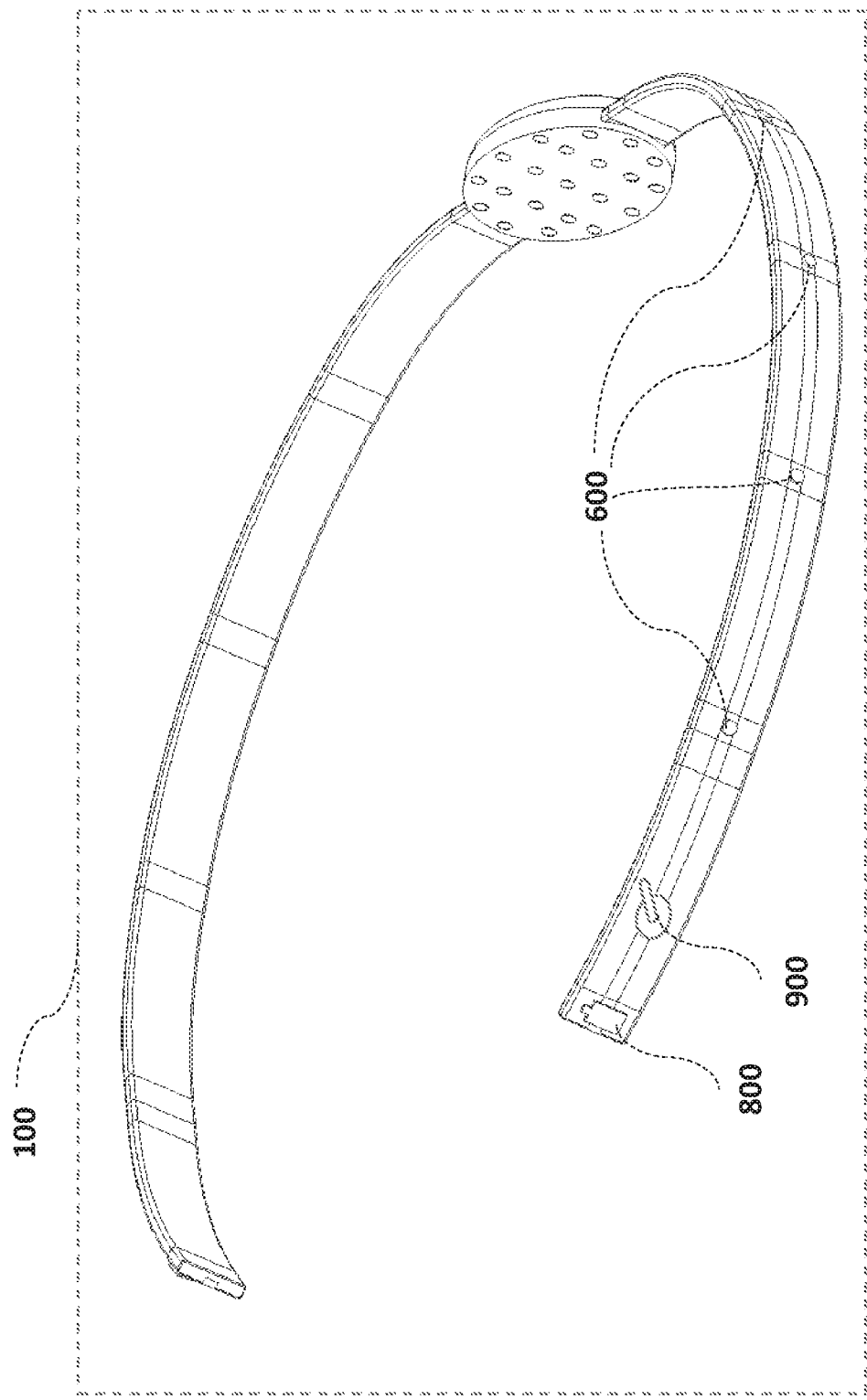
FIG. 2 is another side view of the system of FIG. 1.

Referring now to FIG. 2, the system 100 may further include, for example, indicators 600, a power supply 800, and a switch 900.

Figure 3:
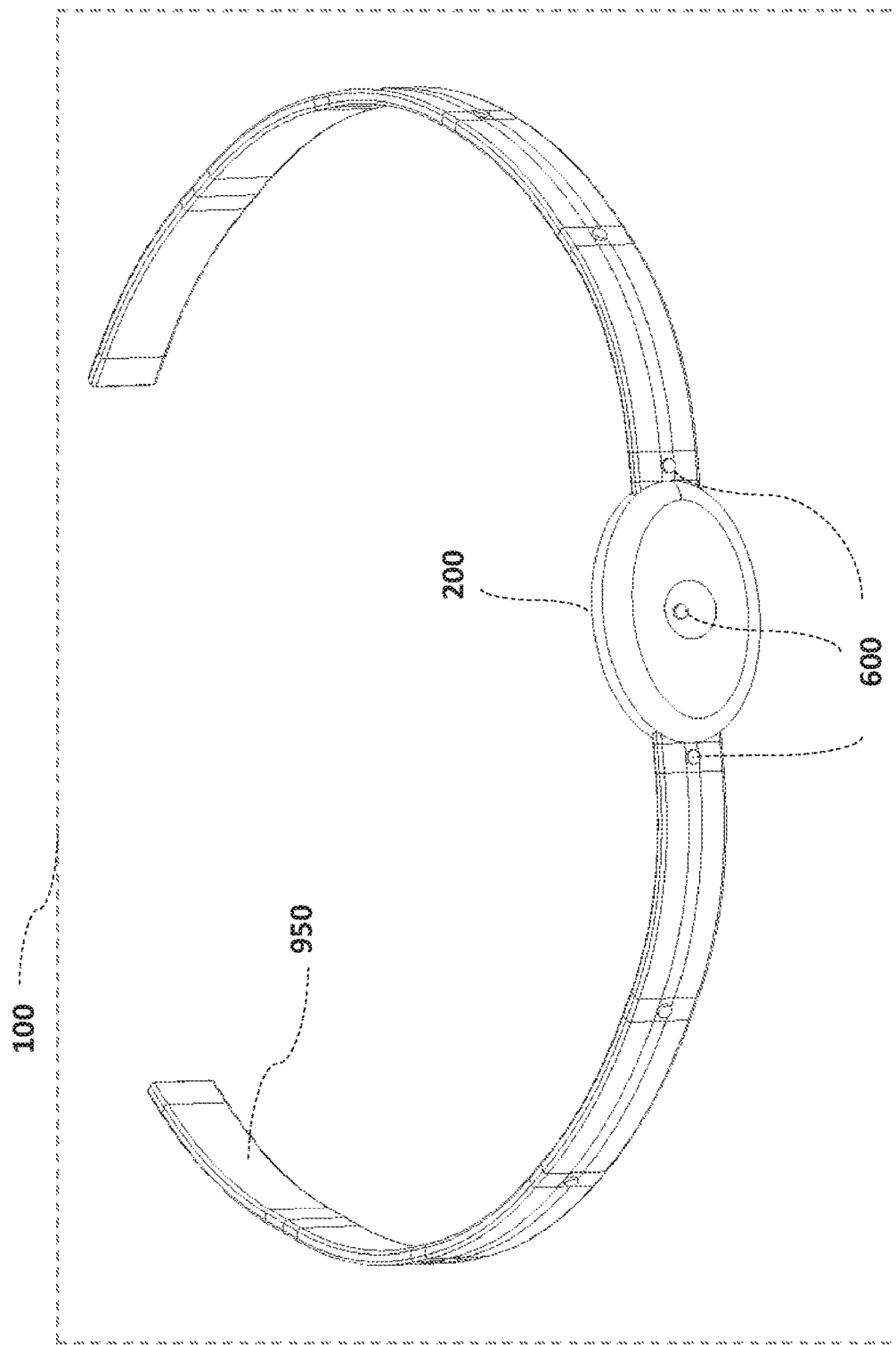
FIG. 3 is a front view of the system of FIG. 1.

Referring now to FIG. 3, the system 100 may further include, for example, indicators 600, and a head band 950.

The neuro connector 200 comprises a base which may be made of an insulating material, for example, plastic. The base supports the set of electrodes 300. The electrodes 300 may be made of a conductive material, for example Sintered Silver-Silver Chloride. The number of electrodes may vary, with 4 to 30 being more typical. The shape of the electrodes 300 may vary with circle being more typically. The width of the electrodes 300 may vary with 1 mm to 5 mm being more typical. The height of the electrodes 300 may vary with 1 mm to 5 mm being more typical. The thickness of the electrodes 300 may vary with 0.1 mm to 5 mm being more typical. The shape of the neuro connector may vary with oval being more typical. The width of the neuro connector 200 may vary with 20 mm to 50 mm being more typical. The height of the neuro connector 200 may vary with 20 mm to 50 mm being more typical. The thickness of the neuro connector 200 may vary with 1 mm to 10 mm being more typical.

The smart chip 400 may comprise a variety of combinations of Central Processing Unit (CPU), Graphics Processing Unit (GPU), memory, and storage device such as a secure digital card (SD card).

The transceiver 500 can transmit signals and receive signals through wired connections, or wireless connections, for example WiFi.

The indicators 600 may be light-emitting diodes (LEDs) or other light emitting devices. The indicators 600 may be used to indicate the modes of system 100, such as on, off, transmitting signals, receiving signals, etc.

The power supply 800 is used to power the system 100. The power supply 800 can be a variety of types such as a lithium ion battery, a zinc-carbon battery, an AC to DC converter, etc. The power supply 800 may supply a variety of voltages with 1.5 to 10 volts being more typical.

The switch 900 is used to turn the system 100 on and off.

The head band 950 is used to hold system 100 on a person's head. The head band 950 may be made of elastic materials such as plastic. The size of the head band 950 may be adjusted so as to fit the user's head comfortably.

The set of conductive wires 700 may be made of low resistance materials, for example, copper. The set of conductive wires 700 connects the power supply, switch, electrodes, indicators, smart chip, and transceiver.

Figure 4:
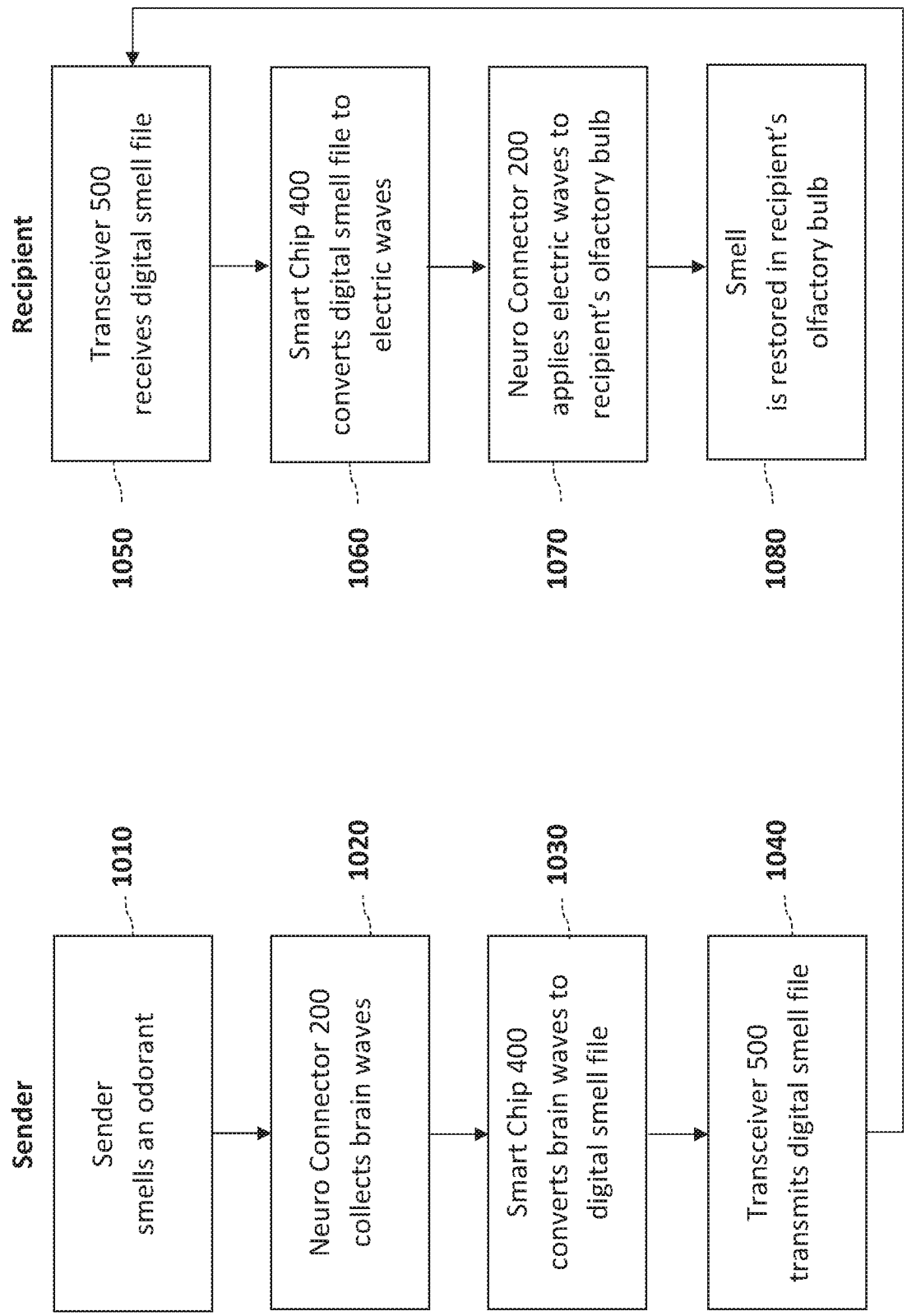
FIG. 4 is a flow chart illustrating an example method in accordance with an aspect of the present disclosure.

FIG. 4 is a flow chart illustrating an example method of transmitting the smell to a remote recipient. A person Sender wears the system 100 on the head so that the neuro connector is over the forehead region over the olfactory bulb, and the electrodes 300 make contact with the skin over the olfactory bulb. A person Recipient wears the system 100 on the head while the neuro connector is over the forehead region over the olfactory bulb, and the electrodes 300 make contact with the skin over the olfactory bulb.

On the Sender's side, the Sender smells an odorant (process 1010). The Sender's olfactory bulb is stimulated by the chemicals from the odorant. The brain waves from the simulation are collected by the neuro connector 200 in the form of electric waves (process 1020). The amplitude of the electric waves may vary with 0.1 mV to 5 mV being more typical. The smart chip 400 converts the electric waves into a digital smell file based on a model, including but not limiting to an electric-to-smell machine learning model (process 1030). The transceiver 500 transmits the digital smell file to the recipient using for example the Internet, Intranet, etc. (process 1040).

On the Recipient side, the transceiver 500 on the system 100 wearing by the recipient receives the digital smell file from the Sender (process 1050). The smart chip 400 extracts the smell identification from the digital smell file. The smart chip 400 converts the smell identification into electric waves based on a model, including but not limiting to a smell-to-electric machine learning model (process 1060). The electric waves are applied to the recipient's olfactory bulb by the electrodes 300 (process 1070). The resulted electric current in the olfactory bulb varies with 0.1 mA to 4 mA being more typical. As a result, the smell of the odorant from the Sender is restored in the recipient (process 1080).

The electric-to-smell machine learning model can be created using a variety of algorithms such as deep learning, support vector machine and Bayes Classification. To create the model, a person wears the system 100. The person is exposed to an odorant which stimulates the person's olfactory bulb. The corresponding brain wave is collected by the electrodes 300 and labelled with that odorant. The person is exposed to the $2^{nd}$ odorant and the corresponding brain waves are collected and labelled with the $2^{nd}$ odorant. The same process repeats for a large number of odorants to create a collection of brain waves with corresponding smell labels. This collection is an electric-to-smell training data set. The training data set is used to train the machine learning algorithms to create the electric-to-smell machine learning model.

In the following claims, the term "neuro connector" referred to above is recited as a "connector" in the claims, and the term "head band" referred to above is recited as "band" in the claims. Also, in the following claims, the term "smart chip" referred to above is recited as a "processor" in the claims.

The smell-to-electric machine learning model can be created using a variety of algorithms such as deep learning, support vector machine and Bayes Classification. To create the model, a person wears the system 100. A set of electric waves is applied to the olfactory bulb through the electrodes 300. The person identify the perceived smell stimulated by the electric waves. The set of electric waves is labelled with that smell. The $2^{nd}$ set of electric waves is applied to the olfactory bulb through the electrodes 300. The person identify the perceived smell stimulated the $2^{nd}$ set of electric waves. The $2^{nd}$ set of electric waves is labelled with the $2^{nd}$ smell. The process is repeated for a large number of electric waves to create a collection of electric waves with corresponding smell labels. This collection is a smell-to-electric training data set. The training data set is used to train the machines learning algorithms to create the smell-to-electric machine learning model.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A system comprising:
    a connector that is configured to collect brain waves from an olfactory bulb of a subject, wherein the olfactory bulb is configured to be stimulated by an odorant for collection of the brain waves, and wherein the connector is also configured to apply electrical current to the olfactory bulb;
    a processor that is configured to convert the brain waves into a digital file, and is configured to convert the digital file into electrical current;
    a transceiver that is configured to transmit the digital file and is configured to receive the digital file;
    a power supply that is configured to provide energy to the system, wherein the power supply, the connector, the processor and the transceiver are electrically connected; and
    a band configured to support the connector, processor, transceiver, and power supply, wherein the band is configured to extend around an exterior of at least a portion of a head of the subject.

2. The system of claim 1, further comprising one or more electrodes configured to contact a portion of the head of the subject in a vicinity of the olfactory bulb.

3. A method of transmitting smell, the method comprising the following steps:
    placing a system of claim 1 on an exterior of a first user's head;
    smelling an odorant by the first user;
    placing a system of claim 1 on an exterior of a second user's head;
    collecting a brain wave with the connector from the first user, wherein the olfactory bulb is configured to be stimulated by the odorant;

converting the brain wave into a digital file with the processor;

transmitting the digital file to the system on the second user's head;

converting, by the processor of the system on the second user's head, the digital file into an electrical current; and applying the electrical current to an area near an olfactory bulb of the second user.

4. The method of transmitting smell of claim 3, the conversion of the brain wave into the digital file is based on at least an electric-to-smell machine learning model.

5. The method of claim 4, wherein the model is trained using the brain waves produced from an olfactory bulb in response to corresponding odorants, and by applying machine learning algorithms.

6. The method of transmitting smell of claim 3, wherein conversion of the digital file into the electrical current is configured to stimulate the olfactory bulb of the second user, and is based on at least a smell-to-electric machine learning model.

7. The method of claim 6, wherein the model is trained using electrical current and the corresponding smells stimulated by the electrical current, and by applying machine learning algorithms.

* * * * *